US005693520A

United States Patent [19]

Branner et al.

[11] Patent Number: 5,693,520
[45] Date of Patent: Dec. 2, 1997

[54] RECOMBINANT TRYPSIN-LIKE PROTEASE

[75] Inventors: Sven Branner, Lyngby; Sven Hastrup, Copenhagen, both of Denmark

[73] Assignee: Novo Nordisk A/S, Bagsvaerd, Denmark

[21] Appl. No.: 553,516

[22] PCT Filed: May 4, 1994

[86] PCT No.: PCT/DK94/00177

§ 371 Date: Nov. 3, 1995

§ 102(e) Date: Nov. 3, 1995

[87] PCT Pub. No.: WO94/25583

PCT Pub. Date: Nov. 10, 1994

[30] Foreign Application Priority Data

May 5, 1993 [DK] Denmark ................... 0523/93

[51] Int. Cl.⁶ ............... C12N 15/77; C12N 9/76; C12N 9/58; C12N 1/15
[52] U.S. Cl. ............ 435/213; 435/223; 435/252.3; 435/252.31; 435/252.33; 435/252.35; 435/254.11; 435/254.2; 435/254.21; 435/254.3; 435/254.7; 435/320.1; 435/172.3; 536/23.2
[58] Field of Search ............. 536/23.2; 435/213, 435/232, 252.3, 252.31, 252.33, 252.35, 254.11, 254.2, 254.21, 254.3, 254.7, 320.1, 172.3

[56] References Cited

FOREIGN PATENT DOCUMENTS

WO 89/06270  2/1989  WIPO.
WO 93/00925  1/1993  WIPO.

OTHER PUBLICATIONS

S.L. Berger et al. (eds.) "Guide to Molecular Cloning Techniques", Meth. Enzymol. 152: 393–399, 415–423, 432–447, 661–704, 1987.

M.P. Deutscher (ed.) "Guide to Protein Purification", Meth. Enzymol. 182: 602–613, 738–751, 1991.

Rypniewski et al, Protein Engineering, vol. 6, No. 4, pp. 341–348, 1993.

Primary Examiner—Rebecca E. Prouty
Attorney, Agent, or Firm—Steve T. Zelson, Esq.; Valeta A. Gregg, Esq.

[57] ABSTRACT

An active recombinant trypsin-like protease enzyme comprising the amino acid residues 25–224 of the amino acid sequence of SEQ ID NO:2, as well as a DNA construct encoding the enzyme and comprising the sequence of SEQ ID NO:1. The enzyme may be used as a detergent enzyme.

13 Claims, 1 Drawing Sheet

FIG. 1

RECOMBINANT TRYPSIN-LIKE PROTEASE

FIELD OF THE INVENTION

The present invention relates to an active recombinant trypsin-like protease, a proteolytic composition comprising said trypsin-like protease, a DNA construct comprising a DNA sequence encoding said trypsin-like protease, and a vector and cell harbouring the DNA construct. Furthermore, the present invention relates to a method of preparing the trypsin-like protease by use of recombinant DNA techniques.

BACKGROUND OF THE INVENTION

Proteases are widely used as ingredients in commercial detergents to improve the detergency towards proteinaceous soiling. For a number of years proteases with a broad specificity, such as subtilisins (Bacillus serine proteases) have been the most widely used detergent proteases. However, in recent years proteases having a more narrow specificity have been of increasing interest for detergent purposes.

WO 89/06270 discloses a detergent composition comprising a protease with a narrow substrate specificity, namely a trypsin-like protease capable of cleaving peptide bonds at the C-terminal side of lysine or arginine. The trypsin-like protease disclosed in said reference is produced by conventional fermentation of a strain of the Fusarium sp. *F. oxysporum* DSM 2672, and is inevitably produced together with another protease (Protease I), the existence of which is undesirable in detergent compositions. Thus, production of the trypsin-like protease from the *F. oxysporum* strain involves a step in which the undesired protease is separated from the trypsin-like protease, which makes the large scale production of the latter protease more expensive than what is desirable.

It would be desirable to facilitate the production of said Fusarium trypsin-like protease, in particular by avoiding the co-production of the above mentioned undesired Protease I, to be able of producing both larger amounts of the enzyme and to produce it in a more economical manner than what is possible by the prior art methods.

BRIEF DISCLOSURE OF THE INVENTION

The present inventors have now succeeded in cloning a DNA sequence encoding a Fusarium trypsin-like protease and in obtaining expression of an active trypsin-like protease from said DNA sequence.

Accordingly, in a first aspect the present invention relates to an active recombinant trypsin-like protease comprising the amino acid residues 1–224 of the amino acid sequence shown in the appended SEQ ID No. 2.

In the present context the term "trypsin-like protease" is intended to indicate an enzyme having an activity similar to that of trypsin, i.e. an enzyme capable of cleaving peptide bonds at the C-terminal side of lysine or arginine. The trypsin-like protease activity may be determined in an assay based on cleavage of a trypsin substrate such as N-Benzoyl-L-arginine-p-nitroanilide hydrochloride (L-BAPA or L-BAPNA), e.g. as described in the Materials and Methods section below.

The term "recombinant" as used about the trypsin-like protease of the invention is intended to indicate that it is produced by a cell transformed with a DNA sequence encoding the protease. Thus, the recombinant trypsin-like protease is produced by another organism than its parent organism and accordingly essentially free from components derived from said parent organism, i.e. components produced by the *F. oxysporum* strain DSM 2672. Such components may confer undesirable properties to the protease, for instance by giving rise to undesirable enzymatic activities. In this respect, the recombinant trypsin-like protease of the invention is easily produced without Protease I, and no costly separation similar to that performed according to WO 89/06270 is required.

In the course of the research leading to the present invention, which is described in detail in the following examples, it was quite unexpectedly found to be difficult to obtain any substantial production of an active trypsin-like protease by cultivation of a conventionally used production organism (*Aspergillus oryzae*) transformed with the DNA sequence shown in SEQ ID No. 1. On the basis of analyses of the DNA sequence and the expression product, it was found that the enzyme encoded by the DNA sequence was expressed as an inactive proenzyme, and that large amounts of this proenzyme were expressed. Thus, even though large amounts of the precursor form of the active enzyme were available no substantial yield of an active maturated enzyme could be obtained, and it was concluded that the proenzyme was unstable in the *A. oryzae* fermentation broth.

It was surprisingly found that the yield of the active recombinant trypsin-like protease could be substantially increased if the medium, in which a host cell harbouring a DNA sequence encoding a proenzyme form of the enzyme was cultivated, also comprised a proteolytic enzyme capable of converting the proenzyme into an active enzyme in situ. It is expected that the low enzymatic activity expressed when no other proteolytic enzyme is present may be ascribed to the fact that the inactive proenzyme form of the trypsin-like protease is considerably unstable and degraded rapidly by proteolytic enzymes expressed from the host organism, and that the addition of a proteolytic enzyme, which more readily than proenzyme-degrading proteolytic enzymes, reacts with the proenzyme resulting in the production of a mature, active trypsin-like protease.

In a further aspect the present invention relates to a DNA construct comprising a DNA sequence encoding an active recombinant trypsin-like protease of the invention as defined above.

In still further aspects the present invention relates to a recombinant expression vector harbouring the DNA construct of the invention, to a cell which either harbours the DNA construct or the expression vector of the invention, and to a process for the production of a trypsin-like protease of the invention, wherein a cell of the invention as described above is cultured under conditions conducive to the production of the protease, and the protease is subsequently recovered from the culture.

Finally, the present invention relates to a detergent additive and detergent composition comprising the active trypsin-like protease of the invention.

DETAILED DESCRIPTION OF THE INVENTION

The amino acid sequence of the recombinant trypsin-like protease of the invention, which was isolated from a strain of the *Fusarium oxysporum* DSM 2672, has been aligned with that of trypsin-like proteases of other origins and have been shown to have a degree of homology of about 43% with that of bovine trypsin (GenBank Acc. No. P00760) and 44% with that of *Streptomyces griseus* (GenBank Acc. No. P00776). The highest homology of the trypsin-like protease of the invention has been observed with that of the fruit fly (GenBank Acc. No. A23493), namely 48%.

These homologies are taken to indicate that some kind of evolutionary relationship exists between trypsin-like proteases, but also that the Fusarium trypsin-like protease of the invention may represent a distinct class of trypsin-like proteases. It is contemplated that the trypsin-like protease of the invention or DNA encoding the protease may be isolated from other organisms, including animals, especially a mammal, an insect, a plant or a microorganism. In the present context, especially interesting origins are bacteria and fungi, including yeasts and filamentous fungi.

The active recombinant trypsin-like protease of the invention comprising the amino acid residues 1–224 of the SEQ ID No. 2 has a number of characteristic properties. For instance, the protease surprisingly shows a reversed Arg/Lys specificity compared to that of bovine trypsin, i.e. the trypsin-like protease of the invention is more Arg-active than Lys-active.

The pH-activity profile of the trypsin-like protease of the invention shows a broad activity optimum between pH 8 and 11, in particular about 10 when using H-D-Val-Leu-Lys-pNA as a substrate at 25° C. The temperature optimum is approximately 40° C. at pH 9.5 using H-D-Val-Leu-Lys-pNA. The mature, active enzyme consists of 224 amino acid residues and has a molecular weight of 22190. It is expressed in the form of a pre-pro-enzyme, in which the signal peptide is contemplated to be amino acid residues –24 to –8 (according to the rules of von Heijne (1986) and the pro-peptide amino acid residues –7 to –1. The specific activity of the enzyme is at least about 30 Casein Protease Units (CPU)/g and preferably equal to or higher than about 35 CPU/g. The protease activity may be determined by the method given in WO 89/06270, the content of which is hereby incorporated by reference.

The DNA sequence of the DNA construct of the invention encoding a recombinant protease enzyme as defined above is preferably as shown in the appended SEQ ID No. 1. Analogues of said sequence, which differ in one or more codons, but which encodes the recombinant protease protein are also within the invention.

The DNA sequence of the DNA construct of the invention may be isolated by well-known methods. Thus, the DNA sequence may, for instance, be isolated by establishing a cDNA or genomic library from an organism expected to harbour the sequence, and screening for positive clones by conventional procedures. Examples of such procedures are hybridization to oligonucleotide probes synthesized on the basis of the full amino acid sequence shown in SEQ ID No. 2 or a subsequence thereof in accordance with standard techniques (cf. Sambrook et al., 1989), and/or selection for clones expressing a trypsin-like protease activity as defined above, and/or selection for clones producing a protein which is reactive with an antibody raised against the trypsin-like protease comprising the amino acid sequence shown in SEQ ID No. 2 and in particular amino acid residues 1–224 thereof.

A preferred method of isolating a DNA construct of the invention from a cDNA or genomic library is by use of polymerase chain reaction (PCR) using degenerate oligonucleotide probes prepared on the basis of the amino acid sequence of the trypsin-like protease of the invention comprising amino acid residues 1–224 of SEQ ID No. 2. For instance, the PCR may be carried out using the techniques described in U.S. Pat. No. 4,683,202 or by R. K. Saiki et al. (1988).

Alternatively, the DNA sequence of the DNA construct of the invention may be prepared synthetically by established standard methods, e.g. the phosphoamidite method described by Beaucage and Caruthers (1981), or the method described by Matthes et al. (1984). According to the phosphoamidite method, oligonucleotides are synthesized, e.g. in an automatic DNA synthesizer, purified, annealed, ligated and cloned in appropriate vectors.

Finally, the DNA construct may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire recombinant DNA molecule, in accordance with standard techniques.

The recombinant expression vector carrying the DNA construct of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA construct of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus Amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase, The expression vector of the invention may also comprise a suitable transcription terminator and, in eukaryotes, polyadenylation sequences operably connected to the DNA sequence encoding the recombinant protease of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Examples of Aspergillus selection markers include amdS, argB, niaD and sC, a marker giving rise to hygromycin resistance. Furthermore, the selection may be accomplished by co-transformation, e.g. as described in WO 91/17243.

While intracellular expression may be advantageous in some respects, e.g. when using certain bacteria as host cells, it is generally preferred that the expression is extracellular. As mentioned above the trypsin-like protease of the invention comprising the amino acid sequence shown in the SEQ ID No. 2 comprises a preregion permitting secretion of the expressed protease into the culture medium. If desirable, this preregion may be substituted with a different preregion or signal sequence, convenient accomplished by substitution of the DNA sequences encoding the respective preregions.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. (1989)).

The cell of the invention either comprising a DNA construct or an expression vector of the invention as defined above is advantageously used as a host cell in the recombinant production of a polypeptide of the invention. The cell may be transformed with the DNA construct of the invention, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of suitable bacteria are grampositive bacteria such as *Bacillus subtilis*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus circulans*, *Bacillus lautus*, *Bacillus megaterium*, *Bacillus thuringiensis*, or *Streptomyces lividans* or *Streptomyces murinus*, or gramnegative bacteria such as *E. coli*. The transformation of the bacteria may for instance be effected by protoplast transformation or by using competent cells in a manner known per se.

The yeast organism may favourably be selected from a species of Saccharomyces or Schizosaccharomyces, e.g. *Saccharomyces cerevisiae*. The filamentous fungus may advantageously belong to a species of Aspergillus, e.g. *Aspergillus oryzae* or *Aspergillus niger*. Alternatively, a strain of a Fusarium species, e.g. *F. oxysporum*, can be used as a host cell. Fungal cells may be transformed by a process involving protoplast formation and transformation of the protoplasts followed by regeneration of the cell wall in a manner known per se. A suitable procedure for transformation of Aspergillus host cells is described in EP 238 023. A suitable method of transforming Fusarium species is described by Malardier et al., 1989.

In a yet further aspect, the present invention relates to a method of producing a recombinant trypsin-like protease of the invention, which method comprises cultivating a host cell as described above under conditions conducive to the production of the protease and recovering the protease from the cells and/or culture medium.

The medium used to cultivate the cells may be any conventional medium suitable for growing the host cell in question and obtaining expression of the protease of the invention. Suitable media are available from commercial suppliers or may be prepared according to published recipes (e.g. in catalogues of the American Type Culture Collection).

From the above disclosure it is apparent that when the trypsin-like protease of the invention is expressed as a proenzyme, substantially increased yields may be obtained when the cultivation is performed in the presence of a proteolytic enzyme or optionally two or more proteolytic enzymes capable of transforming the proenzyme into an active enzyme in the medium.

The proteolytic enzyme(s) may be added as such to the fermentation broth in which the cell producing the proenzyme is cultured. The proteolytic enzyme(s) to be added may be a Bacillus metallo-protease, for instance a commercially available enzyme, e.g. Neutrase®, thermolysin, or another enzyme with a similar activity such as a proteolytic enzyme from *Bacillus stearothermophilus* (Zamost et al., 1990) or an aspartic protease from *F. oxysporum* obtainable as described in Example 1 hereinafter. Alternatively, the proteolytic enzyme may be produced by culturing a host cell transformed with a DNA sequence encoding the proteolytic enzyme under suitable conditions to produce the enzyme and recovering the enzyme from the culture.

Furthermore, the presence of the proteolytic enzyme(s) in the fermentation broth may be accomplished by inserting the DNA sequence(s) encoding said enzyme(s) into the cell harbouring a DNA construct of the invention in such a manner that the proteolytic enzyme(s) is/are expressed and excreted in sufficient amounts to activate the protease of the invention.

The resulting trypsin-like protease may be recovered from the medium by conventional procedures including separating the cells from the medium by centrifugation or filtration, if necessary after disruption of the cells, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

Detergent Composition

According to the invention, the trypsin-like protease may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molar weights of 1000 to 20000, ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as amylase, lipase, cutinase, another protease, cellulase, peroxidase and oxidase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of e.g. the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative as e.g. an aromatic borate ester, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) will usually be neutral or alkaline, e.g. 7–12 such as 7–10.5.

Particular forms of detergent compositions within the scope of the invention include:

1) A detergent composition formulated as a granulate having a bulk density of at least 600 g/l comprising

| | |
|---|---|
| linear alkylbenzenesulfonate (calculated as acid) | 7–12% |
| alcohol ethoxysulfate (e.g. $C_{12-18}$ alcohol, 1-2 EO) or alkyl sulfate (e.g. $C_{16-18}$) | 1–4% |
| alcohol ethoxylate (e.g. $C_{14-15}$ alcohol, 7 EO) | 5–9% |
| sodium carbonate (as $Na_2CO_3$) | 14–20% |
| soluble silicate (as $Na_2O,2SiO_2$) | 2–6% |
| zeolite (as $NaAlSiO_4$) | 15–22% |
| sodium sulfate (as $Na_2SO_4$) | 0–6% |
| sodium citrate/citric acid (as $C_6H_5Na_3O_7/C_6H_8O_7$) | 0–15% |
| sodium perborate (as $NaBO_3.H_2O$) | 11–18% |
| TAED | 2–6% |
| carboxymethylcellulose | 0–2% |
| polymers (e.g. maleic/acrylic acid copolymer, PVP, PEG) | 0–3% |
| enzymes | 0–5% |
| minor ingredients (e.g. suds suppressors, perfume, optical brightener, photobleach) | 0–5% |

2) A detergent composition formulated as a granulate having a bulk density of at least 600 g/l comprising

| | |
|---|---|
| linear alkylbenzenesulfonate (calculated as acid) | 6–11% |
| alcohol ethoxysulfate (e.g. $C_{12-18}$ alcohol, 1-2 EO) or alkyl sulfate (e.g. $C_{16-18}$) | 1–3% |
| alcohol ethoxylate (e.g. $C_{14-15}$ alcohol, 7 EO) | 5–9% |
| sodium carbonate (as $Na_2CO_3$) | 15–21% |
| soluble silicate (as $Na_2O,2SiO_2$) | 1–4% |
| zeolite (as $NaAlSiO_4$) | 24–34% |
| sodium sulfate (as $Na_2SO_4$) | 4–10% |
| sodium citrate/citric acid (as $C_6H_5Na_3O_7/C_6H_8O_7$) | 0–15% |
| carboxymethylcellulose | 0–2% |
| polymers (e.g. maleic/acrylic acid copolymer, PVP, PEG) | 1–6% |
| enzymes | 0–5% |
| minor ingredients (e.g. suds suppressors, perfume) | 0–5% |

3) A detergent composition formulated as a granulate having a bulk density of at least 600 g/l comprising

| | |
|---|---|
| linear alkylbenzenesulfonate (calculated as acid) | 5–9% |
| alcohol ethoxylate (e.g. $C_{12-15}$ alcohol, 7 EO) | 7–14% |
| soap as fatty acid (e.g. $C_{16-22}$) | 1–3% |
| sodium carbonate (as $Na_2CO_3$) | 10–17% |
| soluble silicate (as $Na_2O,2SiO_2$) | 3–9% |
| zeolite (as $NaAlSiO_4$) | 23–33% |
| sodium sulfate (as $Na_2SO_4$) | 0–4% |
| sodium perborate (as $NaBO_3.H_2O$) | 8–16% |
| TAED | 2–8% |
| phosphonate (e.g. EDTMPA) | 0–1% |
| carboxymethylcellulose | 0–2% |
| polymers (e.g. maleic/acrylic acid copolymer, PVP PEG) | 1–3% |
| enzymes | 0–5% |
| minor ingredients (e.g. suds suppressors, perfume, optical brightener) | 0–5% |

4) A detergent composition formulated as a granulate having a bulk density of at least 600 g/l comprising

| linear alkylbenzenesulfonate (calculated as acid) | 8–12% |
|---|---|
| alcohol ethoxylate (e.g. $C_{12-15}$ alcohol, 7 EO) | 10–25% |
| sodium carbonate (as $Na_2CO_3$) | 14–22% |
| soluble silicate (as $Na_2O,2SiO_2$) | 1–5% |
| zeolite (as $NaAlSiO_4$) | 25–35% |
| sodium sulfate (as $Na_2SO_4$) | 0–10% |
| carboxymethylcellulose | 0–2% |
| polymers (e.g. maleic/acrylic acid copolymer, PVP, PEG) | 1–3% |
| enzymes | 0–5% |
| minor ingredients (e.g. suds suppressors perfume) | 0–5% |

5) An aqueous liquid detergent composition comprising

| linear alkylbenzenesulfonate (calculated as acid) | 15–21% |
|---|---|
| alcohol ethoxylate (e.g. $C_{12-15}$ alcohol, 7 EO or $C_{12-15}$ alcohol, 5 EO) | 12–18% |
| soap as fatty acid (e.g. oleic acid) | 3–13% |
| alkenylsuccinic acid ($C_{12-14}$) | 0–13% |
| aminoethanol | 8–18% |
| citric acid | 2–8% |
| phosphonate | 0–3% |
| polymers (e.g. PVP, PEG) | 0–3% |
| borate (as $B_4O_7$) | 0–2% |
| ethanol | 0–3% |
| propylene glycol | 8–14% |
| enzymes | 0–5% |
| minor ingredients (e.g. dispersants, suds suppressors, perfume, optical brightener | 0–5% |

6) An aqueous structured liquid detergent composition comprising

| linear alkylbenzenesulfonate (calculated as acid) | 15–21% |
|---|---|
| alcohol ethoxylate (e.g. $C_{12-15}$ alcohol, 7 EO or $C_{12-15}$ alcohol, 5 EO) | 3–9% |
| soap as fatty acid (e.g. oleic acid) | 3–10% |
| zeolite (as $NaAlSiO_4$) | 14–22% |
| potassium citrate | 9–18% |
| borate (as $B_4O_7$) | 0–2% |
| carboxymethylcellulose | 0–2% |
| polymers (e.g. PEG, PVP) | 0–3% |
| anchoring polymers as e.g. lauryl methacrylate/acrylic acid copolymer; molar ratio 25:1; MW 3800 | 0–3% |
| glycerol | 0–5% |
| enzymes | 0–5% |
| minor ingredients (e.g. dispersants, suds suppressors, perfume, optical brighteners) | 0–5% |

7) A detergent composition formulated as a granulate having a bulk density of at least 600 g/l comprising

| fatty alcohol sulfate | 5–10% |
|---|---|
| ethoxylated fatty acid monoethanolamide | 3–9% |
| soap as fatty acid | 0–3% |
| sodium carbonate (as $Na_2CO_3$) | 5–10% |
| soluble silicate (as $Na_2O,2SiO_2$) | 1–4% |
| zeolite (as $NaAlSiO_4$) | 20–40% |
| sodium sulfate (as $Na_2SO_4$) | 2–8% |
| sodium perborate (as $NaBO_3.H_2O$) | 12–18% |
| TAED | 2–7% |
| polymers (e.g. maleic/acrylic acid copolymer, PEG) | 1–5% |
| enzymes | 0–5% |
| minor ingredients (e.g. optical brightener, suds suppressors, perfume) | 0–5% |

8) A detergent composition formulated as a granulate comprising

| linear alkylbenzenesulfonate (calculated as acid) | 8–14% |
|---|---|
| ethoxylated fatty acid monoethanolamide | 5–11% |
| soap as fatty acid | 0–3% |
| sodium carbonate (as $Na_2CO_3$) | 4–10% |
| soluble silicate (as $Na_2O,2SiO_2$) | 1–4% |
| zeolite (as $NaAlSiO_4$) | 30–50% |
| sodium sulfate (as $Na_2SO_4$) | 3–11% |
| sodium citrate (as $C_6H_5Na_3O_7$) | 5–12% |
| polymers (e.g. PVP, maleic/acrylic acid copolymer, PEG) | 1–5% |
| enzymes | 0–5% |
| minor ingredients (e.g. suds suppressors, perfume) | 0–5% |

9) A detergent composition formulated as a granulate comprising

| linear alkylbenzenesulfonate (calculated as acid) | 6–12% |
|---|---|
| nonionic surfactant | 1–4% |
| soap as fatty acid | 2–6% |
| sodium carbonate (as $Na_2CO_3$) | 14–22% |
| zeolite (as $NaAlSiO_4$) | 18–32% |
| sodium sulfate (as $Na_2SO_4$) | 5–20% |
| sodium citrate (as $C_6H_5Na_3O_7$) | 3–8% |
| sodium perborate (as $NaBO_3.H_2O$) | 4–9% |
| bleach activator (e.g. NOBS or TAED) | 1–5% |
| carboxymethylcellulose | 0–2% |
| polymers (e.g. polycarboxylate or PEG) | 1–5% |
| enzymes | 0–5% |
| minor ingredients (e.g. optical brightener, perfume) | 0–5% |

10) An aqueous liquid detergent composition comprising

| linear alkylbenzenesulfonate (calculated as acid) | 15–23% |
|---|---|
| alcohol ethoxysulfate (e.g. $C_{12-15}$ alcohol, 2-3 EO) | 8–15% |
| alcohol ethoxylate (e.g. $C_{12-15}$ alcohol, 7 EO or $C_{12-15}$ alcohol, 5 EO) | 3–9% |
| soap as fatty acid (e.g. lauric acid) | 0–3% |
| aminoethanol | 1–5% |
| sodium citrate | 5–10% |
| hydrotrope (e.g. sodium toluenesulfonate) | 2–6% |
| borate (as $B_4O_7$) | 0–2% |
| carboxymethylcellulose | 0–1% |
| ethanol | 1–3% |
| propylene glycol | 2–5% |
| enzymes | 0–5% |
| minor ingredients (e.g. polymers, dispersants, perfume, optical brighteners) | 0–5% |

11) An aqueous liquid detergent composition comprising

| linear alkylbenzenesulfonate (calculated as acid) | 20–32% |
|---|---|
| alcohol ethoxylate (e.g. $C_{12-15}$ alcohol, 7 EO or $C_{12-15}$ alcohol, 5 EO) | 6–12% |

-continued

| | |
|---|---|
| aminoethanol | 2–6% |
| citric acid | 8–14% |
| borate (as $B_4O_7$) | 1–3% |
| polymer (e.g. maleic/acrylic acid copolymer, anchoring polymers as e.g. lauryl methacrylate/acrylic acid copolymer and CMC) | 0–3% |
| glycerol | 3–8% |
| enzymes | 0–5% |
| minor ingredients (e.g. hydrotropes, dispersants, perfume, optical brighteners) | 0–5% |

12) A detergent composition formulated as a granulate having a bulk density of at least 600 g/l comprising

| | |
|---|---|
| anionic surfactant (linear alkylbenzenesulfonate, alkyl sulfate, alpha-olefinsulfonate, alpha-sulfo fatty acid methyl esters, alkanesulfonates, soap) | 25–40% |
| nonionic surfactant (e.g. alcohol ethoxylate) | 1–10% |
| sodium carbonate (as $Na_2CO_3$) | 8–25% |
| soluble silicates (as $Na_2O, 2SiO_2$) | 5–15% |
| sodium sulfate (as $Na_2SO_4$) | 0–5% |
| zeolite (as $NaAlSiO_4$) | 15–28% |
| sodium perborate (as $NaBO_3.4H_2O$) | 0–20% |
| bleach activator (TAED or NOBS) | 0–5% |
| enzymes | 0–5% |
| minor ingredients (e.g. perfume, optical brighteners) | 0–3% |

13) Detergent formulations as described in 1)–12) where the content of linear alkylbenzenesulfonate—or a part of it—is substituted by alkyl sulfate ($C_{12}$–$C_{18}$).

14) Detergent formulations as described in 1)–13) which contain a stabilized or encapsulated peracid either as an additional component or as a substitute for already specified bleach systems.

15) Detergent compositions as described in 3), 7), 9) and 12) where the content of perborate is substituted with percarbonate.

16) Detergent composition formulated as a nonaqueous detergent liquid comprising a liquid nonionic surfactant as e.g. linear alkoxylated primary alcohol, a builder system (e.g. phosphate), enzyme and alkali. The detergent may also comprise anionic surfactant and/or a bleach system.

The trypsin-like protease of the invention may be incorporated in concentrations conventionally employed in detergents. It is at present contemplated that, in the detergent composition of the invention, the trypsin-like protease may be added in an amount corresponding to 0.001–100 mg of the enzyme per liter of wash liquor.

BRIEF DESCRIPTION OF THE DRAWINGS

The invention is further illustrated in the accompanying drawings, in which.

The present invention is further illustrated in the following examples which should not, in any manner, be considered to limit the scope of the present invention.

MATERIALS AND METHODS

Strains

*Aspergillus oryzae* IFO 4177

*Fusarium oxysporum* DSM 2672 described in WO 89/06270

*E. coli* MC1000 (Cassabadan and Cohen, 1980)

Determination of trypsin-like Fusarium protease activity

The trypsin-like protease is assayed using the specific substrate N-Benzoyl-Larginine p-nitroanilide hydrochloride (L-BAPA or L-BAPNA).

Buffer 0.01M dimethylglutaric acid (Sigma D4379), 0.2M boric acid and 0.002M calcium chloride adjusted to pH 6.5 with NaOH.

Substrate

L-BAPA is available from Sigma (B3133) or Merck (Art.10754). A 0.2M stock solution in dimethyl sulfoxide is prepared (87 mg/ml) (store frozen) and diluted to 0.004M with the buffer described above.

Assay

The trypsin-like protease is diluted to approx. 15 μg/ml for the assay, 100 μl of the diluted trypsin-like protease are mixed with 100 μl of 0.004M L-BAPA in a 96 well microtiter plate. A blank with 100 μl buffer and 100 μl 0.004 M L-BAPA is used for correction.

The absorption change (delta OD/min) is monitored at 405 nm in an Elisa reader for 10 minutes with readings every 5 minutes at 25° C. or room temperature.

The result is calculated relative to the trypsin content of a reference Fusarium trypsin-like protease.

Plasmids pCDV1-PL (Noma et al., 1986)
p777 (described in EP 0 489 718)
pToC90 (described in WO 91/17243)

EXAMPLES

EXAMPLE 1

Purification of the Trypsin-Like Protease from Fusarium

A crude *F. oxysporum* protease preparation was isolated from the supernatant obtained by fermentation of the *F. oxysporum* DSM 2672 in a soy meal containing medium substantially as described in WO 89/06270. Subsequently, the *Fusarium oxysporum* trypsin-like protease was separated from two other *F. oxysporum* proteases by 0–1M/0–25% sodium chloride/isopropanol gradient elution at pH 7.0 from a bacitracin-silicapolyol affinity column (Mortensen et al., 1989). The two other proteases separated from the *F. oxysporum* trypsin-like protease by this procedure were, a subtilisin-like enzyme, and an aspartic protease with specificity required for the activation of the proform of the *F. oxysporum* trypsin-like protease (Asn-Ile cleavage).

The other purification steps were carried out in accordance with well-known procedures, and included ion exchange chromatography on Separose CL-6B (prior to the bacitracin separation), gelfiltration and concentration by ultrafiltration.

The specific absorption for a 0.1% solution of the purified trypsin-like *F. oxysporum* protease at 280 nm was determined to 1.32.

The purified protease was subsequently subjected to amino acid sequencing and analysis, and the N-terminal amino acid sequence was determined.

EXAMPLE 2

Cloning of a *Fusarium Oxysporum* Trypsin Gene mRNA preparation

Mycelium from a culture of the *F. oxysporum* strain DSM 2672 obtained as described in Example 1 above, was crushed under liquid nitrogen, resuspended in 5M guanidine rhodanide, separated on a CsCl-sarcosyl gradient, and mRNA was isolated therefrom. The mRNA was washed with ethanol, and fractionated on an oligo-dT column (Chirgwin et al. (1978), Truelsen et al. (1979)). The quality of the resulting mRNA was tested in an in vitro translation assay using reticulocyte lysate and $^{35}$S-methionine. An SDS-PAGE analysis showed bands from below 20 to more than 100 kDa.

Preparation and screening of a cDNA library

A cDNA library of the mRNA was constructed in E. coli MC 1000 following the procedure of Noma et al. (1986). After transformation and plating about 15000 colonies were replicated onto Whatman 540 filter paper. A mixed 17-mer probe based on the N-terminal of the enzyme was synthesised ($T_M$ 42°–52° C.)

```
N-terminal:  I VGGTS AGDF PFI VS RNG
             C  C         C        A
Probe:       GATTTCCNTTTATCGT
                            T
```

Split on the isoleucine codons the probe was divided into three pools of 32 and three sets of filters were screened. After wash at 42° C. and re-isolation of possible candidates three positive clones were identified. These positive clones were all found with the ATC-isoleucine probe.

Identification and analysis of the gene

Plasmids were prepared from the three clones according to Sambrook et al, 1989 and, following restriction mapping, two turned out to be identical and the third was about 100 bp shorter. The longer clones were sequenced on both strands using the method of Maxam & Gilbert (1980) and the resulting DNA sequence appears from SEQ ID No. 1.

The amino acid composition of the purified F. oxysporum trypsin-like protease obtained as described in Examples 1 was in accordance with the composition deduced from the DNA-sequence shown in SEQ ID No. 1.

Analysis of this sequence revealed a gene coding for a trypsin-like protease with a 17 amino acid signal peptide according to the rules of von Heijne (1986) (cleaved between Ala-17 and Ala-18) and a propeptide of 7 amino acids (Ala-Pro-Gln-Glu-Ile-Pro-Asn) between the signal peptidase cleavage site and the known N-terminus of the enzyme. The role of this hypothetical propeptide is unknown but proteases are normally made as inactive zymogens.

The mature enzyme shows less than 50% identity with all known trypsins be it mammalian, from fruit fly, or bacterial (Streptomyces). The highest identity (48%) of the mature trypsin-like protease was found with a fruit fly trypsin.

Figure 1:
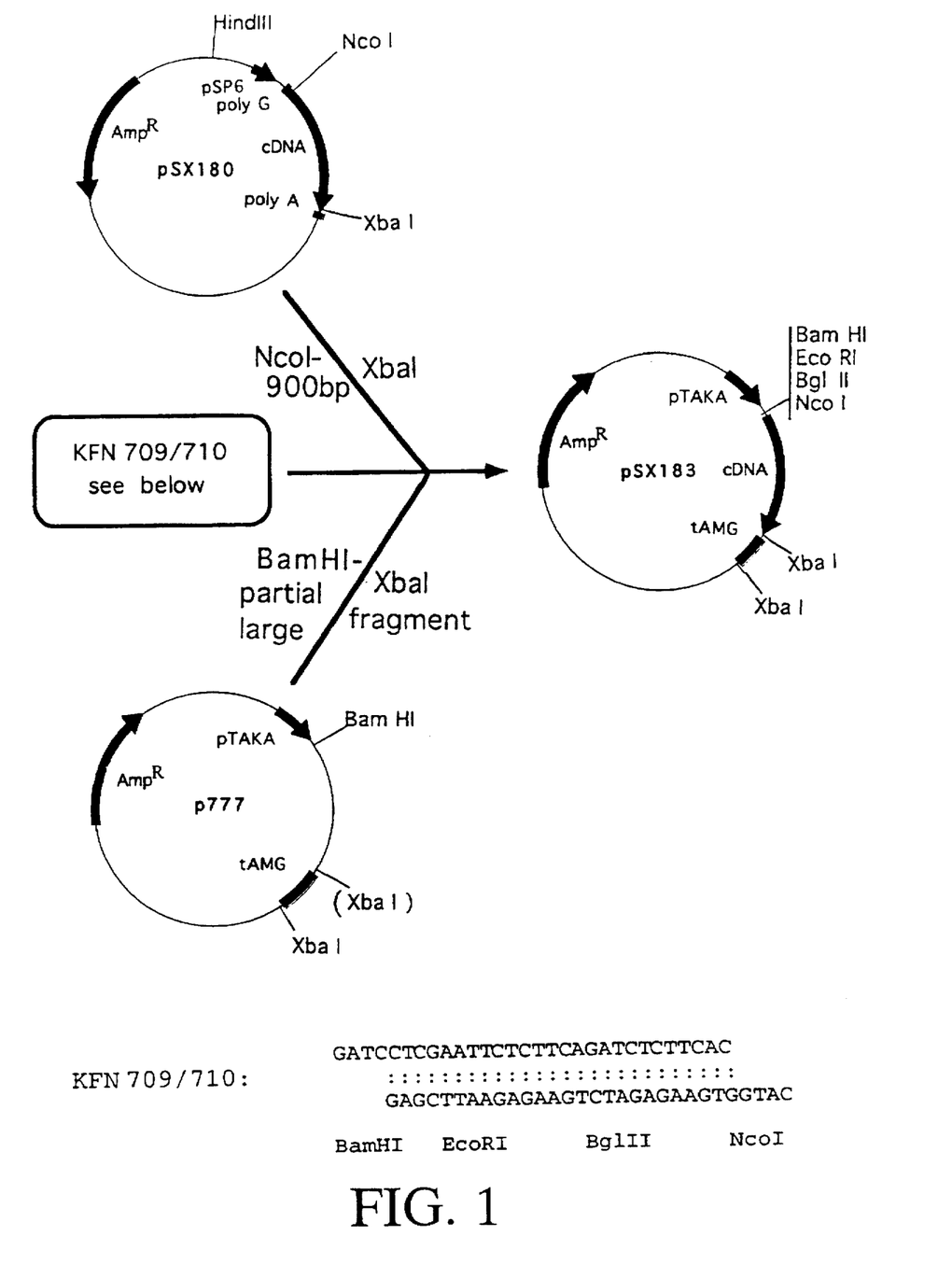
FIG. 1 illustrates the construction of the expression plasmid pSX183 further described in Example 3.

Expression of the gene product cDNA encoding the trypsin-like F. oxysporum protease, obtained as described above, was inserted into the vector pCDV1-PL described by Noma et al. (1986) resulting in the plasmid pSX180. The coding region of the cDNA was inserted as a NcoI-XbaI fragment into the Aspergillus expression plasmid p777 (EP 0 489 718) which was cut with BamHI and partially with XbaI. To join thê 5'end of the cloned DNA to the vector a synthetic linker DNA KFN709/710 (illustrated in FIG. 1) was added to the ligation reaction. The resulting plasmid pSX183 was co-transformed into A. oryzae (IFO 4177) together with plasmid pToC90 carrying the amdS from A. nidulans (WO 91/17243). Transformants were selected for growth on acetamide. When grown in YPD medium a protein appeared in the supernatant slightly larger than the trypsin-like protease isolated from F. oxysporum supernatants. Surprisingly no activity of the gene product could be determined from hydrolysis of L-Benzoyl-Arginoyl-pNA (a trypsin substrate).

EXAMPLE 3

Activation of the Proenzyme

In an attempt to obtain an active trypsin-like protease, an aspartyl protease isolated from F. oxysporum supernatants (as described in Example 1) was added to the fermentation medium harbouring the inactive trypsin-like protease.

By this treatment it was found that the protein from the transformed A. oryzae became the same size as the standard on an SDS gel and the sample showed tryptic activity as determined form hydrolysis of L-Benzoyl-Arginoyl-pNA (data not shown). This indicates that the enzyme is expressed in the form of a proenzyme, and thus confirms the presence of a propeptide as deduced from the DNA sequence. From the activity studies it is apparent that the function of the propeptide is to keep the enzyme in an inactive form.

REFERENCES CITED IN THE SPECIFICATION

Chirgwin, J. M., Przybyla, A. E., MacDonald, R. J., and Rutter, W. J. (1978). Isolation of biologically active ribonucleic acid from sources enriched in ribonuclease. Biochemistry 18:5294–5299.

Truelsen, E., Gausing, K., Jochimsen, B., Jorgensen, P., and Marcker, K. A. (1979). Cloning of soybean leghemoglobin structural gene sequences synthesized in vitro. Nucleic Acids Res. 6:3061–3072.

Christensen, T., Woeldike, H., Boel, E., Mortensen, S. B., Hjortshoej, K., Thim, L., and Hansen, M. T. (1988). High level expression of recombinant genes in Aspergillus oryzae. Bio/Technology 6:1419–1422.

Maxam, A. M., and Gilbert, W. (1980). Sequencing end-labelled DNA with base-specific chemical cleavages. Methods Enzymol. 65:499- von Heijne, G. (1986). A new method for predicting signal sequence cleavage sites. Nucleic Acids Res. 14:4683–4690.

Hudson, L., and Hay, F. Practical Immunology, Third edition (1989), Blackwell Scientific Publications Lipman and Pearson, Science 227, 1435 (1985)

Sambrook et at., Molecular Cloning: A Laboratory Manual, 2nd Ed., Cold Spring Harbor, 1989

Saiki, R. K. et al., Science 239, 1988, pp. 487–491, 1988

Beaucage et at., Tetrahedron Letters 22, 1981, pp. 1859–1869

Matthes et al., The EMBO J. 3, 1984, pp. 801–805

Malardier et al., Gene 78 (1989), pp. 147–156

Zamost et al., Journal of Industrial Microbiology, Vol. 5, pp. 303–312, 1990

Noma et al. (1986), Nature 319, 640–646

Cassabadan and Cohen (1980), J. Mol. Biol. 138, 179–203

We claim:

1. A DNA construct comprising the DNA sequence of SEQ ID NO:1.

2. A DNA construct according to claim 1, wherein the DNA sequence is as shown in the appended SEQ ID No. 1.

3. A recombinant expression vector comprising the DNA construct of claim 1.

4. A cell comprising the DNA construct of claim 1.

5. The cell of claim 4, wherein the cell is a microbial cell.

6. The cell of claim 5, wherein the cell is a bacterial cell or a fungal cell.

7. The cell of claim 6, in which the bacterial cell is a cell of a gram-positive bacterium or a cell of a gram-negative bacterium and the fungal cell is a yeast cell or a cell of a filamentous fungus.

8. A method of producing a recombinant protease enzyme, wherein a cell containing the DNA construct of claim 1 is cultured under conditions conducive to the production of the protease, and the protease is subsequently recovered from the culture.

9. The method of claim 8, wherein the recombinant protease enzyme is expressed in the form of a proenzyme and the cell is—cultured in the presence of a proteolytic enzyme capable of converting the proenzyme of the protease into a mature enzyme.

10. The method of claim 8, wherein the proteolytic enzyme is a metallo-protease.

11. A cell comprising the vector of claim 3.

12. The cell of claim 7, in which the gram-positive bacterium is Bacillus or Streptomyces, the gram-negative bacterium is Escherichia, the yeast cell is Saccharomyces, and the filamentous fungus is Aspergillus or Fusarium.

13. The method of claim 10, wherein the proteolytic enzyme is a Bacillus metallo-protease.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 998 base pairs
        ( B ) TYPE: nucleic acid
        ( C ) STRANDEDNESS: single
        ( D ) TOPOLOGY: linear     ( i x ) FEATURE:
        ( A ) NAME/KEY: CDS
        ( B ) LOCATION:130..801

( i x ) FEATURE:
        ( A ) NAME/KEY: mat_peptide
        ( B ) LOCATION:58..801

( x i ) SEQUENCE DESCRIPTION: SEQ ID NO: 1:

```
ATCATCAACC ACTCTTCACT CTTCAACTCT CCTCTCTTGG ATATCTATCT CTTCACCATG      60

GTCAAGTTCG CTTCCGTCGT TGCACTTGTT GCTCCCCTGG CTGCTGCCGC TCCTCAGGAG     120

ATCCCCAAC ATT GTT GGT GGC ACT TCT GCC AGC GCT GGC GAC TTT CCC         168
          Ile Val Gly Gly Thr Ser Ala Ser Ala Gly Asp Phe Pro
           1               5                  10

TTC ATC GTG AGC ATT AGC CGC AAC GGT GGC CCC TGG TGT GGA GGT TCT       216
Phe Ile Val Ser Ile Ser Arg Asn Gly Gly Pro Trp Cys Gly Gly Ser
     15              20                  25

CTC CTC AAC GCC AAC ACC GTC TTG ACT GCT GCC CAC TGC GTT TCC GGA       264
Leu Leu Asn Ala Asn Thr Val Leu Thr Ala Ala His Cys Val Ser Gly
 30              35                  40                  45

TAC GCT CAG AGC GGT TTC CAG ATT CGT GCT GGC AGT CTG TCT CGC ACT       312
Tyr Ala Gln Ser Gly Phe Gln Ile Arg Ala Gly Ser Leu Ser Arg Thr
             50                  55                  60

TCT GGT GGT ATT ACC TCC TCG CTT TCC TCC GTC AGA GTT CAC CCT AGC       360
Ser Gly Gly Ile Thr Ser Ser Leu Ser Ser Val Arg Val His Pro Ser
                 65                  70                  75

TAC AGC GGA AAC AAC AAC GAT CTT GCT ATT CTG AAG CTC TCT ACT TCC       408
Tyr Ser Gly Asn Asn Asn Asp Leu Ala Ile Leu Lys Leu Ser Thr Ser
             80                  85                  90

ATC CCC TCC GGC GGA AAC ATC GGC TAT GCT CGC CTG GCT GCT TCC GGC       456
Ile Pro Ser Gly Gly Asn Ile Gly Tyr Ala Arg Leu Ala Ala Ser Gly
         95                  100                 105

TCT GAC CCT GTC GCT GGA TCT TCT GCC ACT GTT GCT GGC TGG GGC GCT       504
Ser Asp Pro Val Ala Gly Ser Ser Ala Thr Val Ala Gly Trp Gly Ala
110                 115                 120                 125

ACC TCT GAG GGC GGC AGC TCT ACT CCC GTC AAC CTT CTG AAG GTT ACT       552
Thr Ser Glu Gly Gly Ser Ser Thr Pro Val Asn Leu Leu Lys Val Thr
             130                 135                 140

GTC CCT ATC GTC TCT CGT GCT ACC TGC CGA GCT CAG TAC GGC ACC TCC       600
Val Pro Ile Val Ser Arg Ala Thr Cys Arg Ala Gln Tyr Gly Thr Ser
                 145                 150                 155

GCC ATC ACC AAC CAG ATG TTC TGT GCT GGT GTT TCT TCC GGT GGC AAG       648
Ala Ile Thr Asn Gln Met Phe Cys Ala Gly Val Ser Ser Gly Gly Lys
         160                 165                 170

GAC TCT TGC CAG GGT GAC AGC GGC GGC CCC ATC GTC GAC AGC TCC AAC       696
Asp Ser Cys Gln Gly Asp Ser Gly Gly Pro Ile Val Asp Ser Ser Asn
     175                 180                 185

ACT CTT ATC GGT GCT GTC TCT TGG GGT AAC GGA TGT GCC CGA CCC AAC       744
Thr Leu Ile Gly Ala Val Ser Trp Gly Asn Gly Cys Ala Arg Pro Asn
```

-continued

| | | | | | | | | | | | | | | | | |
|---|---|---|---|---|---|---|---|---|---|---|---|---|---|---|---|---|
|190| | | |195| | | |200| | | |205| | | | |
|TAC|TCT|GGT|GTC|TAT|GCC|AGC|GTT|GGT|GCT|CTC|CGC|TCT|TTC|ATT|GAC|792|
|Tyr|Ser|Gly|Val|Tyr|Ala|Ser|Val|Gly|Ala|Leu|Arg|Ser|Phe|Ile|Asp| |
| | | |210| | | | |215| | | | |220| | | |
|ACC|TAT|GCT|TAAATACCTT|GTTGGAAGCG|TCGAGATGTT|CCTTGAATAT| | | | | | | | | |841|
|Thr|Tyr|Ala| | | | | | | | | | | | | | |
|TCTCTAGCTT|GAGTCTTGGA|TACGAAACCT|GTTGAGAAA|TAGGTTTCAA|CGAGTTAAGA| | | | | | | | | | |901|
|AGATATGAGT|TGATTTCAGT|TGGATCTTAG|TCCTGGTTGC|TCGTAATAGA|GCAATCTAGA| | | | | | | | | | |961|
|TAGCCCAAAT|TGAATATGAA|ATTTGATGAA|AATATTC| | | | | | | | | | | | |998|

( 2 ) INFORMATION FOR SEQ ID NO: 2:

( i ) SEQUENCE CHARACTERISTICS:
      ( A ) LENGTH: 224 amino acids
      ( B ) TYPE: amino acid
      ( D ) TOPOLOGY: linear ( i i ) MOLECULE TYPE: protein ( x i ) SEQUENCE DESCRIPTION: SEQ ID NO: 2:

```
Ile Val Gly Gly Thr Ser Ala Ser Ala Gly Asp Phe Pro Phe Ile Val
 1               5                  10                  15

Ser Ile Ser Arg Asn Gly Gly Pro Trp Cys Gly Gly Ser Leu Leu Asn
            20                  25                  30

Ala Asn Thr Val Leu Thr Ala Ala His Cys Val Ser Gly Tyr Ala Gln
        35                  40                  45

Ser Gly Phe Gln Ile Arg Ala Gly Ser Leu Ser Arg Thr Ser Gly Gly
    50                  55                  60

Ile Thr Ser Ser Leu Ser Ser Val Arg Val His Pro Ser Tyr Ser Gly
65                  70                  75                  80

Asn Asn Asn Asp Leu Ala Ile Leu Lys Leu Ser Thr Ser Ile Pro Ser
                85                  90                  95

Gly Gly Asn Ile Gly Tyr Ala Arg Leu Ala Ala Ser Gly Ser Asp Pro
            100                 105                 110

Val Ala Gly Ser Ser Ala Thr Val Ala Gly Trp Gly Ala Thr Ser Glu
        115                 120                 125

Gly Gly Ser Ser Thr Pro Val Asn Leu Leu Lys Val Thr Val Pro Ile
    130                 135                 140

Val Ser Arg Ala Thr Cys Arg Ala Gln Tyr Gly Thr Ser Ala Ile Thr
145                 150                 155                 160

Asn Gln Met Phe Cys Ala Gly Val Ser Ser Gly Gly Lys Asp Ser Cys
                165                 170                 175

Gln Gly Asp Ser Gly Gly Pro Ile Val Asp Ser Ser Asn Thr Leu Ile
            180                 185                 190

Gly Ala Val Ser Trp Gly Asn Gly Cys Ala Arg Pro Asn Tyr Ser Gly
        195                 200                 205

Val Tyr Ala Ser Val Gly Ala Leu Arg Ser Phe Ile Asp Thr Tyr Ala
    210                 215                 220
```